(12) United States Patent
Park et al.

(10) Patent No.: US 11,034,664 B1
(45) Date of Patent: Jun. 15, 2021

(54) SYNTHESIS OF CYCLIC CARBONATE MONOMERS

(71) Applicant: International Business Machines Corporation, Armonk, NY (US)

(72) Inventors: Nathaniel H. Park, San Jose, CA (US); James L. Hedrick, Pleasanton, CA (US); Victoria A Piunova, Los Gatos, CA (US); Pedro Arrechea, San Jose, CA (US); Tim Erdmann, San Jose, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 16/871,733

(22) Filed: May 11, 2020

(51) Int. Cl.
   *C07D 319/06* (2006.01)

(52) U.S. Cl.
   CPC .................... *C07D 319/06* (2013.01)

(58) Field of Classification Search
   CPC .................................................... C07D 319/06
   USPC ......................................................... 549/228
   See application file for complete search history.

(56) References Cited

U.S. PATENT DOCUMENTS

| | | | |
|---|---|---|---|
| 9,303,056 | B2 | 4/2016 | Kataoka |
| 2012/0095166 | A1 | 4/2012 | Ward et al. |
| 2015/0183777 | A1 | 7/2015 | Yael et al. |
| 2019/0153019 | A1 | 5/2019 | Hedrick et al. |

FOREIGN PATENT DOCUMENTS

| | | | |
|---|---|---|---|
| CN | 106543153 | A | 3/2017 |
| CN | 106749159 | A | 5/2017 |
| CN | 109608572 | A | 4/2019 |
| CN | 110981847 | * | 4/2020 |
| WO | 2009/102795 | A1 | 8/2009 |
| WO | 2014015056 | A2 | 1/2014 |
| WO | 2015/005901 | A1 | 1/2015 |

OTHER PUBLICATIONS

Tan et al , Towards Automated Monomer synthesis: : A Streamlined Approach for the synthesis of Cyclic Carbonates Chem Rxiv , Jan. 1-19, 2020 (Year: 2020).*
Bag, et al. "Kinetics of Ion Transport in Perovskite Active Layers and Its Implications for Active Layer Stability."Venkataraman, S. et al. J. Am. Chem. Soc., 2015, 137, 851. 11 pages.

(Continued)

*Primary Examiner* — Taylor V Oh

(74) *Attorney, Agent, or Firm* — Amin, Turocy & Watson, LLP

(57) ABSTRACT

Techniques regarding the synthesis of cyclic carbonate monomers are provided. For example, one or more embodiments described herein can comprise a method, which can include cyclizing a functionalized diol monomer with N,N'-carbonyldiimidazole, wherein the cyclizing produces a cyclic carbonate monomer and an imidazole carbamate. The method can also include activating the imidazole carbamate with an acid, wherein the activating promotes cyclization of the imidazole carbamate into the cyclic carbonate monomer.

19 Claims, 13 Drawing Sheets

(56) References Cited

OTHER PUBLICATIONS

Venkataraman, et al. "2-Amino-1,3-propane diols: a versatile platform for the synthesis of aliphatic cyclic carbonate monomers." Polym. Chem., 2013, 4, 2945. 4 pages.
Zhang, et al. "Fast and selective ring-opening polymerizations by alkoxides and thioureas." Nat. Chem, 2016, 8, 1047. 7 pages.
Lin, et al. "Urea Anions: Simple, Fast, and Selective Catalysts for Ring-Opening Polymerizations." R. M. J. Am. Chem. Soc. 2017, 139, 1645. 8 pages.
Kamber, et al. "Organocatalytic Ring-Opening Polymerization." Chem. Rev., 2007, 107, 5813. 28 pages.
Sanders, et al. "A simple and efficient synthesis of functionalized cyclic carbonate monomers using a versatile pentafluorophenyl ester intermediate." J. Am. Chem. Soc. 2010, 132, 14724. 3 pages.
Chan, et al. "Tetra-n-butylammonium Fluoride as an Efficient Transesterification Catalyst for Functionalizing Cyclic Carbonates and Aliphatic Polycarbonates." ACS Macro Lett. 2013, 10, 860. 5 pages.
Zeng, et al. "Hyperbranched Aliphatic Polyester via Cross-Metathesis Polymerization: Synthesis and Postpolymerization Modification." Macromolecular Rapid Communications 2018, 39 (5), 1700658. 7 pages.
Anonymous "Polymers and compositions." IP.com, IPCOM000201038D, Nov. 5, 2010. 93 pages.
Suriano, et al. "Functionalized cyclic carbonates: from synthesis and metal-free catalyzed ring-opening polymerization to applications." Polymer Chemistry, 2(3), 528-533, Sep. 24, 2010. 14 pages.
Mindemark, et al. "Synthesis and Polymerization of Alkyl Halide-Functional Cyclic Carbonates." Polymer 2011, 52 (25), 5716-5722. 7 pages.
Olsson, et al. "Reactive imidazole intermediates: simplified synthetic approach to functional aliphatic cyclic carbonates." M. Polym. Chem. 2014, 5 (23), 6651-6655. 5 pages.
Mespouille, et al. "Implementation of metal-free ring-opening polymerization in the preparation of aliphatic polycarbonate materials." Progress in Polymer Science, 39(6), 1144-1164, 2014. 21 pages.

\* cited by examiner

1002 — SELECTIVELY REACTING A PRIMARY ALCOHOL GROUP OF A DIOL MONOMER WITH CDI AND AN AMINE BASE, WHEREIN THE SELECTIVELY REACTING FORMS A CARBAMATE AMINE SALT COMPOUND

1004 — CYCLIZING THE CARBAMATE AMINE SALT COMPOUND WITH AN ACID, WHEREIN THE CYCLIZING FORMS A CYCLIC CARBONATE MONOMER

1006 — FUNCTIONALIZING THE CYCLIC CARBONATE MONOMER VIA AN ESTERIFICATION OF A CARBOXYL GROUP OF THE CYCLIC CARBONATE MONOMER

SYNTHESIS OF CYCLIC CARBONATE MONOMERS

BACKGROUND

The subject disclosure relates to the synthesis of cyclic carbonate monomers, and more specifically, to the synthesis of cyclic carbonate monomers and/or functionalized cyclic carbonate monomers from various diol monomers using an alkylation-cyclization and/or cyclization-esterification processes.

Aliphatic polycarbonates are a privileged polymer platform for precision biomedical applications. Their excellent biocompatibility and the broad scope of functional groups that may be incorporated on polymer backbone have enabled a multitude of uses; such as antimicrobial, therapeutic, and/or high-performance materials. Of the many cyclic carbonate monomers reported, those derived from bis-methoxy propionic acid ("bis-MPA") can be versatile scaffolds. This is due to the shear number of diverse functional groups that can be appended to the monomer. In turn, these functional groups impart unique properties to the resultant polymer, which can be principally accessed through controlled ring-opening polymerization. These enabling factors, in combination with the inexpensive and wide availability of the bis-MPA starting material, make this class of carbonates an ideal platform for the development of new applications for degradable materials with highly tailored properties.

The principal issues in any synthetic approach to bis-MPA based carbonate monomer is the installment of the desired functional group on the pendant ester and the cyclization of the 1,3-diol into the cyclic carbonate. To accomplish this, conventional approaches rely on protection-deprotection schemes to enable selective transformations, although necessitating additional steps. Other conventional approaches utilized the selective alkylation of the carboxylic acid followed by cyclization to afford the desired carbonate monomer. However, the alkylation conditions are often harsh and would be incompatible with highly base-sensitive substrates. Additionally, the conventional approaches require the use of triphosgene or chloroformate reagents (e.g., toxic reagents) to achieve cyclization to the carbonate; oftentimes in substantial excess. The resulting monomers often require repeated purification as small impurities from the cyclization step can trigger slow oligomerization of the carbonate monomer.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, methods that can facilitate the synthesis of cyclic carbonate monomers are described.

According to an embodiment, a method is provided. The method can comprise cyclizing a functionalized diol monomer with N,N'-carbonyldiimidazole, wherein the cyclizing can produce a mixture of a cyclic carbonate monomer and an imidazole carbamate product. The method can also comprise activating the imidazole carbamate product with an acid, wherein the activating can promote cyclization of the imidazole carbamate product into the cyclic carbonate monomer. An advantage to such a method can be the use of reagents that can be readily handled and/or can exhibit low toxicity.

In some examples, the method can further comprise reacting a diol monomer using a base compound, wherein the reacting promotes functionalization of the diol monomer with a substrate having a reactive functional group. An advantage of such a method can be the synthesis of cyclic carbonate monomers with a wide variety of available functional groups.

According to another embodiment, a method is provided. The method can comprise selectively reacting a primary alcohol group of a diol monomer with N,N'-carbonyldiimidazole and an amine base, wherein the selectively reacting can form a carbamate amine salt compound. The method can also comprise cyclizing the carbamate amine salt compound with an acid, wherein the cyclizing can form a cyclic carbonate monomer. An advantage of such a method can be the synthesis of a non-functionalized cyclic carbonate monomer using reagents that do not require anhydrous and/or cryogenic conditions and/or an inert atmosphere.

In some examples, the diol monomer is 3-hydroxy-2-(hydroxymethyl)-2-methylpropanoic acid. An advantage of such a method can be enabled use of readily available regents to synthesis target cyclic carbonate monomers.

According to another embodiment, a method is provided. The method can comprise adding an amine base and N,N'-carbonyldiimidazole to a solution of a diol monomer, wherein the adding the amine base and N,N'-carbonyldiimidazole can form a carbamate amine salt. The method can also comprise adding an acid to a solution of the amine salt, the adding the acid can form a cyclic carbonate monomer via cyclization. An advantage of such a method can be the synthesis of cyclic carbonate monomers via a synthesis that exhibits a short reaction time (e.g., thereby facilitating scaling of the synthesis protocols).

In some examples, the method can also comprise functionalizing the cyclic carbonate monomer via an esterification of a carboxyl group of the cyclic carbonate monomer. An advantage of such a method can be the ability to synthesis a broad spectrum of cyclic carbonate monomers with various functionalities.

BRIEF DESCRIPTION OF THE DRAWINGS

FIG. 10 illustrates a flow diagram of an example, non-limiting method that can facilitate the synthesis of a cyclic carbonate monomer via a cyclization-esterification process in accordance with one or more embodiments described herein.

DETAILED DESCRIPTION

Figure 1:
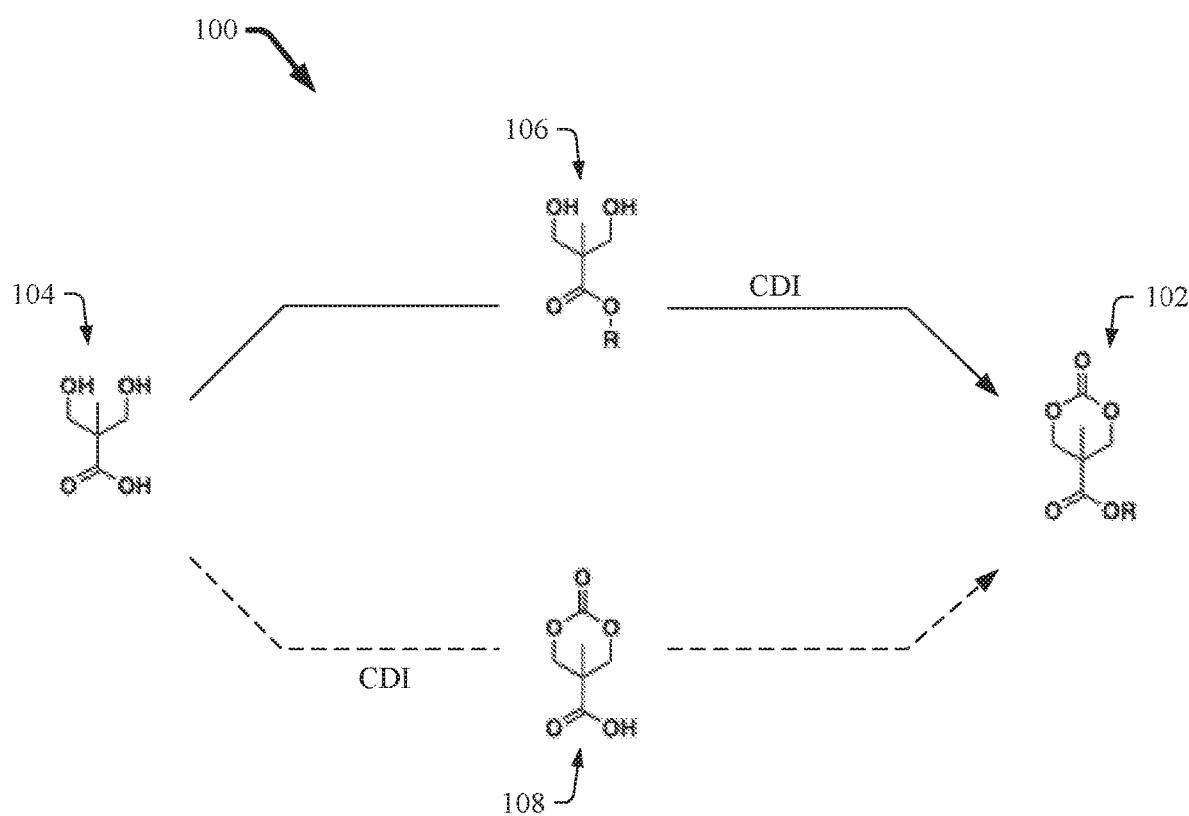
FIG. 1 illustrates a diagram of an example, non-limiting synthesis scheme that can facilitate the synthesis of a cyclic carbonate monomer via an alkylation-cyclization and/or cyclization-esterification process in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Given the problems with other approaches to synthesizing cyclic carbonate monomers; the present disclosure can be implemented to produce a solution to one or more of these problems by synthesizing a cyclic carbonate monomer via an alkylation-cyclization and/or cyclization-esterification process using CDI. Advantageously, one or more embodiments described herein can achieve improved conditions for the synthesis of carbonate monomers via a two-step process without the use of hazardous phosgene or chloroformate reagents. Further, the carbonate monomer can be obtained in excellent yields and often without the need for chromatographic purification. Various embodiments described herein can enable rapid access to a broad scope of functional groups on the carbonate monomer, which in turn can be readily polymerized to their corresponding polycarbonates.

One or more embodiments described herein can regard the synthesis of cyclic carbonate monomers via one or more alkylation-cyclization processes and/or cyclization-esterification processes. For example, one or more alkylation-cyclization processes can comprise selectively functionalizing a carboxyl group of a diol monomer (e.g., bis-MPA) prior to cyclization with CDI. In another example, one or more cyclization-esterification processes can comprise selectively cyclizing a diol monomer (e.g., bis-MPA) and functionalizing the resulting cyclic carbonate monomer via esterification of a carboxyl group with one or more coupling agents. Various embodiments described herein can utilize CDI as a cyclization agent with short reaction times.

The various exemplary experiment procedures described herein can be setup under an air atmosphere with benchtop solvents unless otherwise noted. CDI can be purchased from Aldrich or Oakwood Chemical and used as received. The bulk of the CDI can either be stored in a nitrogen-filled glovebox or on the benchtop, protected from ambient moisture. The CDI can be assayed for purity by proton ("$^1$H") NMR in deuterated chloroform ("CDCl$_3$") and the equivalents for the cyclization reactions can be adjusted accordingly.

The various NMR spectra described herein can be collected at room temperature using a Bruker Avance NMR Spectrometer operating at 400 megahertz (MHz). All $^{13}$C and $^{19}$F NMR spectra can be collected at room temperature using the same instrument operating at 100 and 376 MHz, respectively. $^1$H and $^{13}$C NMR spectra can be referenced to the internal residual solvent signal (e.g., 7.26 parts per million (ppm) and 77.16 ppm, respectively for CDCl$_3$). Gel permeation chromatography ("GPC") measurements can be performed using a Waters Advanced Polymer Chromatography with tetrahydrofuran ("THF") as the eluent at 25 degrees Celsius (° C.) or a Waters system equipped with four 5 micron (μm) columns (300 millimeter (mm)×7.7 mm) connected in series (e.g., with increasing pore sizes: 100, 1000, 105, 10$^6$ Å) and a Waters 410 differential refractometer, with a flow rate of 1.0 milliliters per minute (mL/min) (e.g., in THF). GPC instruments can be calibrated with polystyrene standards. Infrared measurements can be done on neat samples using a Thermo Scientific Nicolet iS5 with an iD7 ATR-diamond.

FIG. 1 illustrates an example, non-limiting synthesis scheme 100 of functionalized cyclic carbonate monomers 102 that can be implemented via one or more alkylation-cyclization processes and/or cyclization-esterification processes in accordance with one or more embodiments described herein. Repetitive description of like elements employed in other embodiments described herein is omitted for sake of brevity. As shown in FIG. 1, the one or more alkylation-cyclization processes can be delineated by a solid arrow, and the one or more cyclization-esterification processes can be delineated by a dashed arrow.

The one or more alkylation-cyclization processes (e.g., delineated by a solid arrow in FIG. 1) can comprise synthesizing one or more functionalized cyclic carbonate monomers 102 from one or more diol monomers 104 via an alkylation and a cyclization. For example, during an alkylation of the one or more alkylation-cyclization processes a diol monomer 104 can be functionalized with one or more pendent functional groups (e.g., represented by "R" in FIG. 1) to form one or more functionalized diol monomers 106. Further, during a cyclization of the one or more alkylation-cyclization processes the one or more functionalized diol monomers 106 can undergo a carbonate formation promoted by CDI to synthesize one or more functionalized cyclic carbonate monomers 102.

Additionally, the one or more cyclization-esterification processes (e.g., delineated by a dashed arrow in FIG. 1) can comprise synthesizing the one or more functionalized cyclic carbonate monomers 102 from one or more diol monomers 104 via a cyclization and an esterification. For example, during a cyclization of the one or more cyclization-esterification processes the one or more diol monomers 104 can undergo a carbonate formation promoted by CDI to form one or more non-functionalized cyclic carbonate monomers 108. Further, during an esterification of the one or more cyclization-esterification processes a carboxyl group of the non-functionalized cyclic carbonate monomers 108 can be selectively functionalized with one or more functional groups (e.g., represented by "R" in FIG. 1) to form the one or more functionalized cyclic carbonate monomers 102.

One of ordinary skill in the art will recognize that the chemical compounds depicted in FIG. 1 are exemplary and that the features of the one or more alkylation-cyclization and/or cyclization-esterification processes described herein can be applied to a variety of chemical compounds to synthesize the functionalized cyclic carbonate monomers 102. For example, FIG. 1 depicts bis-MPA as the one or more diol monomers 104; however, other diol monomer 104 structures are also envisaged. In one or more embodiments, monomers comprising at least two hydroxyl groups and one or more carboxyl groups can be the one or more diol monomers 104. Diol monomers 104 comprising at least two hydroxyl groups but no carboxyl groups are also envisaged. Example monomers that can be the one or more diol monomers 104 can include, but are not limited to: 2,2-bis(hydroxymethyl)butyric acid, 2,2-bis(hydroxymethyl)acetic acid, dimethyl bis(hydroxymethyl)malonate, cis-butenediol, 1,3-propane diol, N-methyldiethanolamine, N-phenyldiethanolamine, trimethylolethane, 2-(hydroxymethyl)propane-1,3-diol, 2-ethyl-2-(hydroxymethyl)propane-1,3-diol, 2-methyl-1,4-butanediol, 1,4-pentanediol, 1,3-butanediol, a combination thereof, and/or the like.

Example functional groups (e.g., represented by "R" in FIG. 1) that can serve as pendent functional groups for the one or more functionalized diol monomers 106 and/or functionalized cyclic carbonate monomers 102 can include, but are not limited to: alkyl groups, benzyl groups, phenyl groups, amino groups, guanidinium groups, urea groups, sulphate groups, phosphate groups, thioether groups, ether groups, alkene groups, alkyne groups, alkyl halide groups, benzyl halide groups, amide groups, sulfonamide groups, heterocyclic arene groups, heterocyclic groups, a combination thereof, and/or the like. For instance, the one or more functional groups can be derived from one more substrates including, but not limited to: alkyl halides, benzylic halides, allylic halides, sulfonates, carbonates, esters, carbamates, phosphonates, a combination thereof, and/or the like. In another instance, the one or more functional groups can be derived from one or more alcohols.

Figure 2:
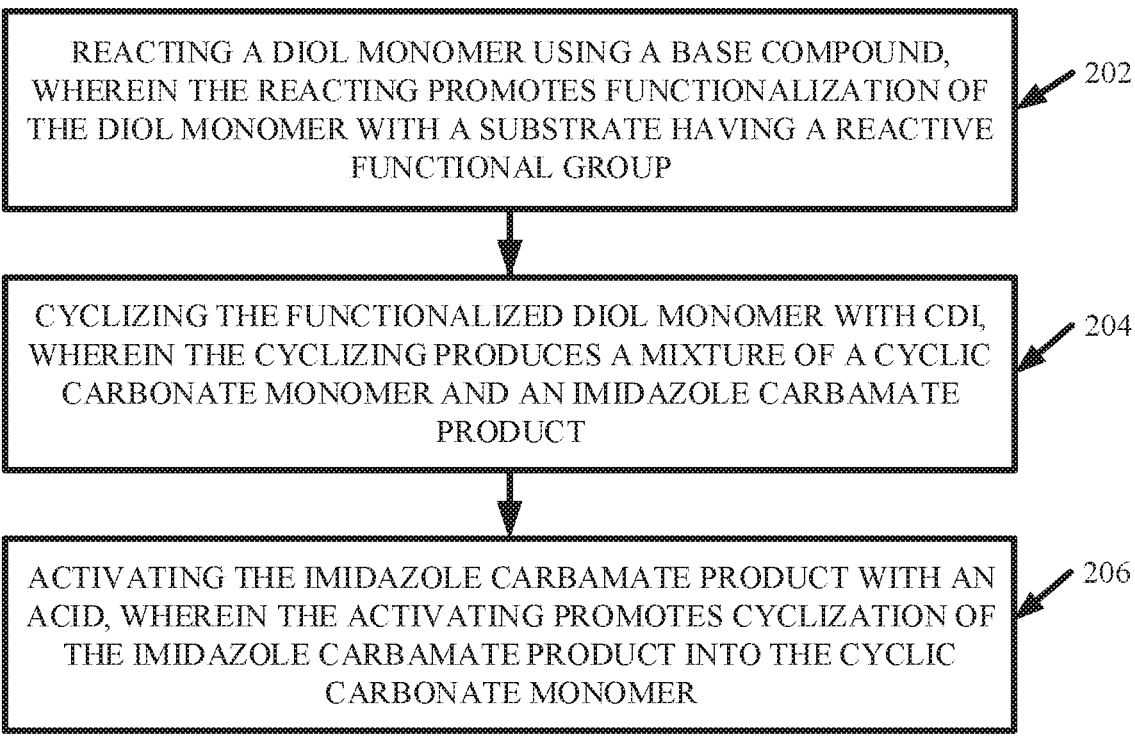
FIG. 2 illustrates a flow diagram of an example, non-limiting method that can facilitate the synthesis of a cyclic carbonate monomer via an alkylation-cyclization process in accordance with one or more embodiments described herein.

FIG. 2 illustrates a flow diagram of an example, non-limiting method 200 that can facilitate synthesizing the one or more functionalized cyclic carbonate monomers 102 via the one or more alkylation-cyclization processes in accordance with one or more embodiments described herein. Repetitive description of like elements employed in other embodiments described herein is omitted for sake of brevity.

At 202, the method 200 can comprise reacting one or more diol monomers 104 using a base compound, wherein the reacting at 202 can promote functionalization of the one or more diol monomers 104 with a substrate having a reactive functional group. In various embodiments, the reacting at 202 can be performed during an alkylation of the one or more alkylation-cyclization processes described herein. For example, the reacting at 202 can form the one or more functionalized diol monomers 106. In various embodiments, example base compounds can include, but are not limited to: an amine base, a carbonate base, a phosphate base, a hydroxide base, an alkoxide base, a combination thereof, and/or the like. Also, example substrates with reactive functional groups that can facilitate functionalization of the one or more diol monomers 104 can include, but are not limited to: alkyl halides, benzylic halides, allylic halides, sulfonates, carbonates, esters, carbamates, phosphonates, a combination thereof, and/or the like.

At 204, the method 200 can comprise cyclizing the one or more functionalized diol monomers 106 with CDI, wherein the cyclizing at 204 can produce a mixture of one or more functionalized cyclic carbonate monomers 102 and/or imidazole carbamate products. In various embodiments, the cyclizing at 204 can be performed during a cyclization of the one or more alkylation-cyclization processes described herein. In one or more embodiments, the one or more imidazole carbamate products can be formed as intermediates. Product distribution of the functionalized cyclic carbonate monomers 102 and imidazole carbamate products formed at 204 can be readily shifted based on the equivalents of CDI, rate of addition of CDI, and/or concentration of the reagents.

At 206, the method 200 can further comprise activating the one or more imidazole carbamate products with one or more acids, wherein the activating at 206 can promote cyclization of the one or more imidazole carbamate products into the one or more functionalized cyclic carbonate monomers 102. In various embodiments, the activating at 206 can be performed during the cyclization of the one or more alkylation-cyclization processes described herein. In one or more embodiments, the one or more imidazole carbamate products can be subjected to acidic conditions to further increase the yield of the functionalized cyclic carbonate monomer 102. Advantageously, the method 200 can synthesize the functionalized cyclic carbonate monomer 102 in high yields without anhydrous conditions, cryogenic conditions, and/or toxic reagents.

Figure 3A:
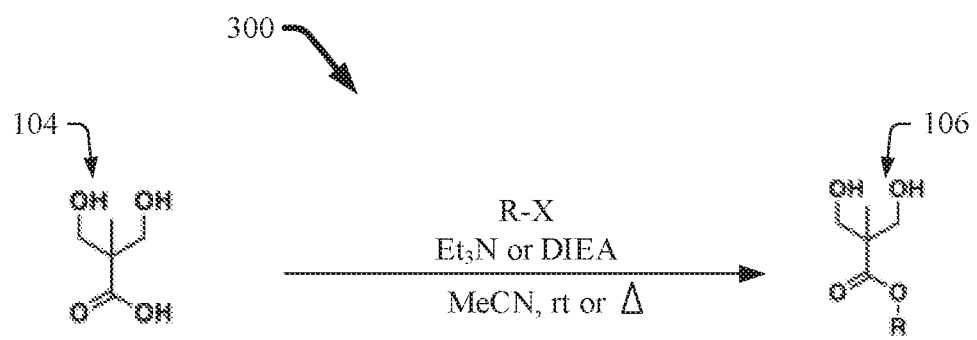
FIG. 3A illustrates a diagram of an example, non-limiting alkylation scheme that can be comprised within an alkylation-cyclization process for the synthesis of cyclic carbonate monomers in accordance with one or more embodiments described herein.

FIG. 3A illustrates a diagram of an example, non-limiting alkylation scheme 300 that can be performed during one or more alkylation-cyclization processes to facilitate synthesis of one or more functionalized cyclic carbonate monomers 102 in accordance with one or more embodiments described herein. Repetitive description of like elements employed in other embodiments described herein is omitted for sake of brevity. In various embodiments, the exemplary alkylation scheme 300 can be performed during functionalization at 202 of method 200.

FIG. 3A depicts the exemplary alkylation scheme 300 with regards to bis-MPA as the diol monomer 104; however, as described herein, the use of other monomers as the diol monomer 104 is also envisaged. Alkylation scheme 300 exemplifies how the one or more diol monomers 104 can undergo an alkylation to form the one or more functionalized diol monomers 106. As shown in FIG. 3A, during alkylation, the carboxyl group of the diol monomer 104 (e.g., bis-MPA) can be selectively alkylated in the presence of two primary alcohols. In various embodiments, the alkylation can be facilitated by one or more organic amine bases and one or more solvents. Example organic amine bases that can be utilized in the alkylation scheme 300 can include, but are not limited to: triethylamine ("Et$_3$N"), diisopropylethylamine ("DIEA"), 1,1,3,3-tetramethylguanidine, 1,8-diazabicyclo (5.4.0)undec-7-ene,1,5-diazabicyclo(4.3.0)non-5-ene, 2-tert-butyl-1,1,3,3-tetramethylguanidine, N,N-dicyclohexylmethylamine,N,N-diethylmethylamine, a combination thereof, and/or the like. Example solvents that can be utilized in the alkylation scheme 300 can include, but are not limited to: acetonitrile ("MeCN"), ethyl acetate, acetone, butyl acetate, isopropyl acetate, N,N-dimethylformamide, N,N-dimethylacetamide, dimethyl sulfoxide, N-methyl-2-pyrrolidone, N-cyclohexyl-2-pyrrolidone, cyclohexanone, dichloroethane, propylene carbonate, tetrahydrofuran, cyclopentyl methyl ether, dimethoxy ethane, a combination thereof, and/or the like. As shown in FIG. 3A, the alkylation scheme 300 can be performed at room temperature ("rt") and/or at an elevated temperature ("Δ").

For example, the one or more amine bases can enable functionalization of the one or more diol monomers 104 with one or more substrates having a reactive functional group (e.g., alkyl, benzylic, or allylic halides and/or alcohols). For instance, the one or more substrates having a reactive functional group (e.g., alkyl, benzylic, or allylic halides and/or alcohols) can be represented by "R-X" in FIG. 3A; wherein "R" can represent one or more reactive functional groups (e.g., alkyl groups, benzyl groups, and/or allylic groups) that can become pendent functional groups as a result of the functionalization. Also, "X" can represent one or more halides, sulfonates, carbonates, esters, carbamates, phosphonates, and/or hydroxyl groups. Example substrates with reactive functional groups (e.g., represented by "R-X" in FIG. 3A) that can functionalize the one or more diol monomers 104 can include, but are not limited to: α,α'-dichloro-p-xylene, benzyl bromide, pentafluorobenzyl bromide, tert-butyl chloroacetate, ethanol, 1-bromooctane, 1-bromododecane,2-(2-(2-methoxyethoxy)ethoxy)ethyl4-methylbenzenesulfonate, 1-iodobutane, 2-bromopropane, tert-butyl 4-(bromomethyl)benzoate, a combination thereof, and/or the like.

The following experimental procedure can exemplify implementation of the alkylation scheme 300. A flask can be equipped with a magnetic stir-bar and charged with bis-MPA (e.g., 1 equivalent) and MeCN (e.g., 0.5 molar (M)). The suspension can be stirred at room temperature and DIEA (e.g., 1.05 equivalents) can be added. The reaction mixture can be stirred until it had become completely homogenous (e.g., about 5 minutes) and the alkylating agent was added (e.g., 1 equivalent). The flask can be equipped with a reflux condenser and heated to the indicated temperature in a pre-heated oil bath until the reaction had reached full conversion as determined by $^1$H NMR analysis of the crude reaction mixture. Once complete, the reaction mixture was removed from the oil bath and allowed to cool to room temperature. The solvent can then be removed with the aid of the rotary evaporator and the crude residue can be dissolved in ethyl acetate ("EtOAc") (e.g., 50 mL) and poured into 1 M hydrochloric acid ("HCl") (e.g., 100 mL). The phases were separated, and the aqueous layer can be extracted twice more with EtOAc (e.g., 50 mL). The combined organic layers can be dried over magnesium sulfate ("MgSO$_4$"), filtered, and concentrated with the aid of a rotary evaporator.

Figure 3B:
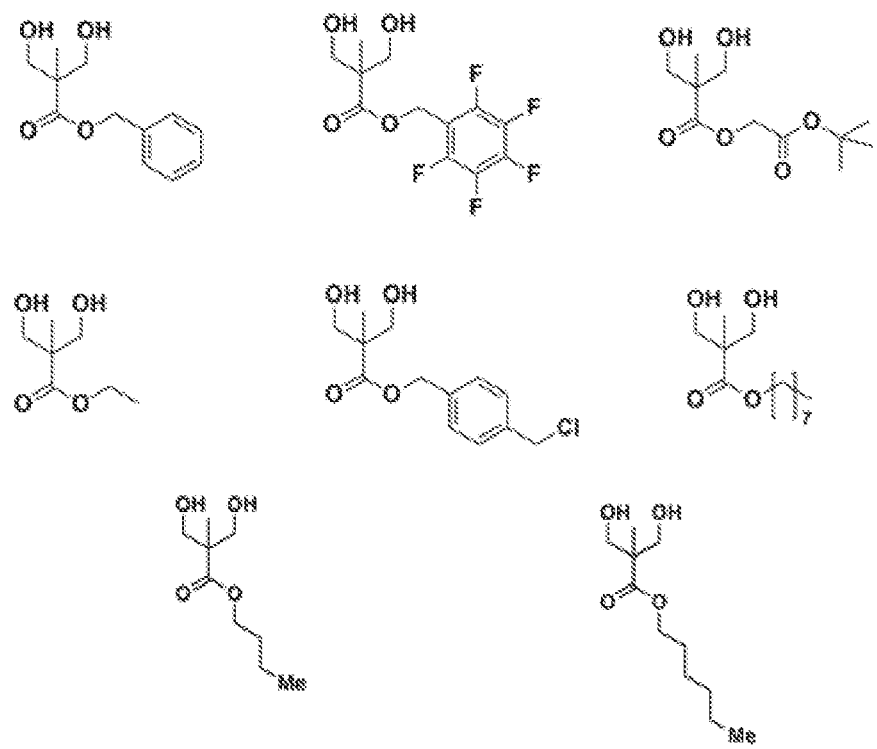
FIG. 3B illustrates a diagram of example, non-limiting functionalized diol monomers that can be synthesized by the alkylation scheme in accordance with one or more embodiments described herein.

FIG. 3B illustrates a diagram of example, non-limiting functionalized diol monomer 106 structures that can be achieved via the alkylation scheme 300 in accordance with one or more embodiments described herein. Repetitive description of like elements employed in other embodiments described herein is omitted forsake of brevity. As shown in FIG. 3B, some exemplary functionalized diol monomer 106 structures can include, but are not limited to: MPA-benzyl ("MPA-Bn"), MPA-benzyl fluoride ("BnFs"), 2-(tert-butoxy)-2-oxoethyl 3-hydroxy-2-(hydroxymethyl)-2-methylpropanoate, MPA-ethyl ("MPA-Et"), MPA-benzyl chloride ("MPA-Cl"), MPA-octyl, and/or the like. One of ordinary skill in the art will recognize that the architecture of the functionalized diol monomers 106 is not so limited; for example, additional chemical structures for the functionalized diol monomers 106 are also envisaged. As demonstrated by the exemplary structures shown in FIG. 3 B, the alkylation scheme 300 can facilitate functionalization of the one or more diol monomers 104 with a wide variety of functional groups.

Figure 4A:
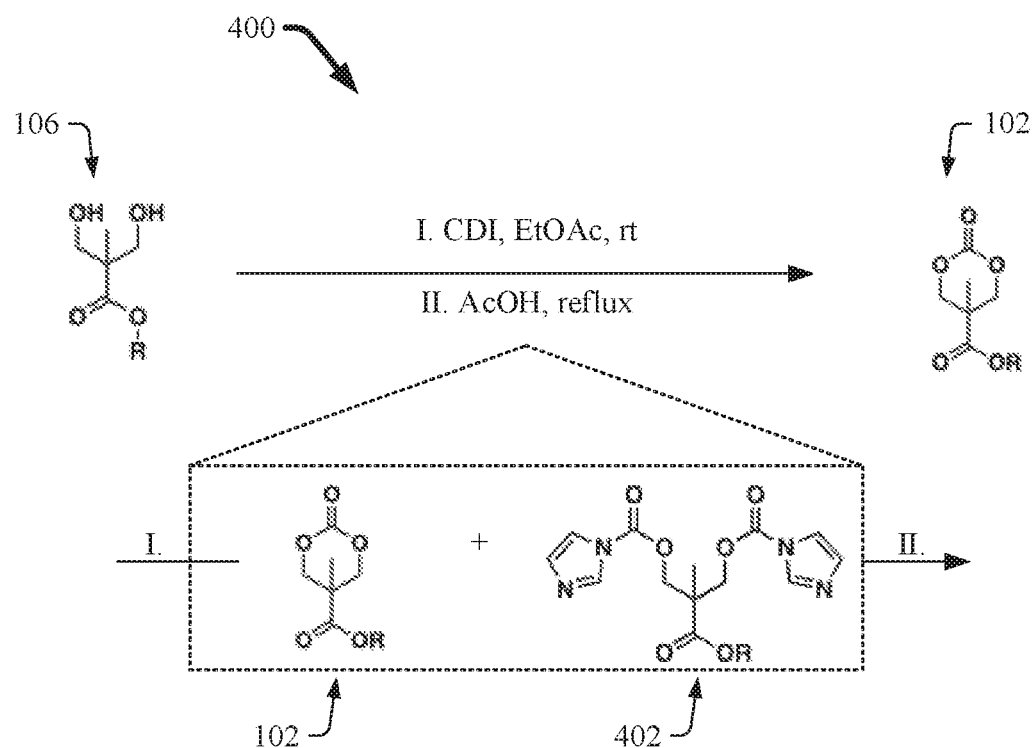
FIG. 4A illustrates a diagram of an example, non-limiting first cyclization scheme that can be comprised within an alkylation-cyclization processes for the synthesis of cyclic carbonate monomers using N,N'-carbonyldiimidazole ("CDI") in accordance with one or more embodiments described herein.

FIG. 4A illustrates a diagram of an example, non-limiting first cyclization scheme 400 that can be performed during one or more alkylation-cyclization processes to facilitate synthesis of one or more functionalized cyclic carbonate monomers 102 in accordance with one or more embodiments described herein. Repetitive description of like elements employed in other embodiments described herein is omitted forsake of brevity. In various embodiments, the exemplary first cyclization scheme 400 can be performed during the cyclizing at 204 and/or activating at 206 of method 200.

As shown in FIG. 4A, the first cyclization scheme 400 can utilize CDI to facilitate carbonate formation. Advantageously, CDI can exhibit an ease of handling, low toxicity, and an ability to remove imidazole byproducts. In various embodiments, the first cyclization scheme 400 can comprise a first stage (e.g., represented by "I." in FIG. 4) where CDI is added to a solution of the one or more functionalized diol monomers 106 (e.g., dissolved in EtOAc at room temperature). An amount of CDI added to the functionalized diol monomer 106 solution can range, for example, from greater than or equal to 1.0 equivalents to less than or equal to 3 equivalents (e.g., 1.5 equivalents). In one or more embodiments, the CDI can be added over a period of time ranging, for example, from greater than or equal to 1 second to less than or equal to 60 minutes. The first stage of the first cyclization scheme 400 can form two products: the one or more functionalized cyclic carbonate monomers 102, and one or more imidazole carbamate monomers 402. The product distribution exhibited by the first stage of the first cyclization scheme 400 can be controlled by adjusting the equivalents of CDI, the rate of CDI addition, and/or the concentration of the reagents.

Further, in order to avoid unnecessary purification of significant quantities of byproduct from the functionalized cyclic carbonate monomers 102, a second stage (e.g., represented by "II." In FIG. 4A) of the first cyclization scheme 400 can convert the one or more imidazole carbamate monomers 402 into further yields of the functionalized cyclic carbonate monomers 102. During the second stage of the cyclization scheme 400 the one or more imidazole carbamate monomers 402 can be activated with excess amounts of acid to promote conversion of the imidazole carbamate monomers 402 to the functionalized cyclic carbonate monomers 102. Example acids that can be used in the second stage of the first cyclization scheme 400 to promote conversion of the one or more imidazole carbamate monomers 402 can include, but are not limited to: acetic acid ("AcOH"), benzoic acid, trifluoroacetic acid, hydrochloric acid, methanesulfonic acid, p-tolylsulfonic acid pyridinium salt, formic acid, maleic acid, phosphoric acid, trimethylsilyl trifluoromethanesulfonate, a combination thereof, and/or the like. One of ordinary skill in the art will recognize that the amount of acid added to the one or more imidazole carbamate monomers 402 can vary depending on the type of acid utilized. An example amount of added acid (e.g., AcOH) can be greater than or equal to 0.1 equivalents and less then or equal to 30 equivalents (e.g., 4 equivalents).

In various embodiments, the one or more functionalized cyclic carbonate monomers 102 can be readily isolated in high purity following an aqueous workup. Further purification via crystallization, filtration through a silica gel plug, or chromatographic separation can be conducted to ensure complete removal of trace impurities that may promote slow decomposition of the functionalized cyclic carbonate monomer 102 via oligomerization.

The following experimental procedure can exemplify implementation of the first cyclization scheme 400. A flask can be equipped with a magnetic stir-bar and charged with the functionalized diol monomers 106 (e.g., 1 equivalent), MeCN (e.g., about 0.5 M in starting material), and the reaction mixture was stirred at room temperature until the functionalized diol monomer 106 had fully dissolved. CDI (e.g., 1.5 equivalents) can then be added and the reaction was stirred at room temperature for 5 min (e.g., additional small amounts of CDI (e.g., about 0.25 equivalents) can be added to ensure full conversion of the starting functionalized diol monomer 106 as determined by $^1$H NMR). AcOH (e.g., 16 equivalents) can then be added to the reaction mixture and the reaction mixture can be equipped with a reflux condenser and heated to 75° C. for 1-3 hours in a pre-heated oil bath.

After full conversion as determined by $^1$H NMR, the reaction mixture can be removed from the oil bath, cooled to room temperature, and then concentrated with the aid of a rotary evaporator. The crude residue can be dissolved in EtOAc (e.g., 100 mL) and poured into 2M HCl (e.g., 100 mL). The organic and aqueous phases were separated, and the aqueous phase was extracted further with EtOAc (2×100 mL). The combined organic layers can be dried over MgSO$_4$, filtered, and concentrated. The resulting residue can then be dissolved in a mixture of EtOAc (e.g., 50 mL) and toluene ("PhMe")(e.g., 50 mL) and concentrated using a rotary evaporator to remove the AcOH. The isolated material can be purified by dissolution in a minimal amount of EtOAc. Hexanes can be added to this solution to induce crystallization. The crystals can then be collected via vacuum filtration and washed with additional hexane to afford the desired product.

Figure 4B:
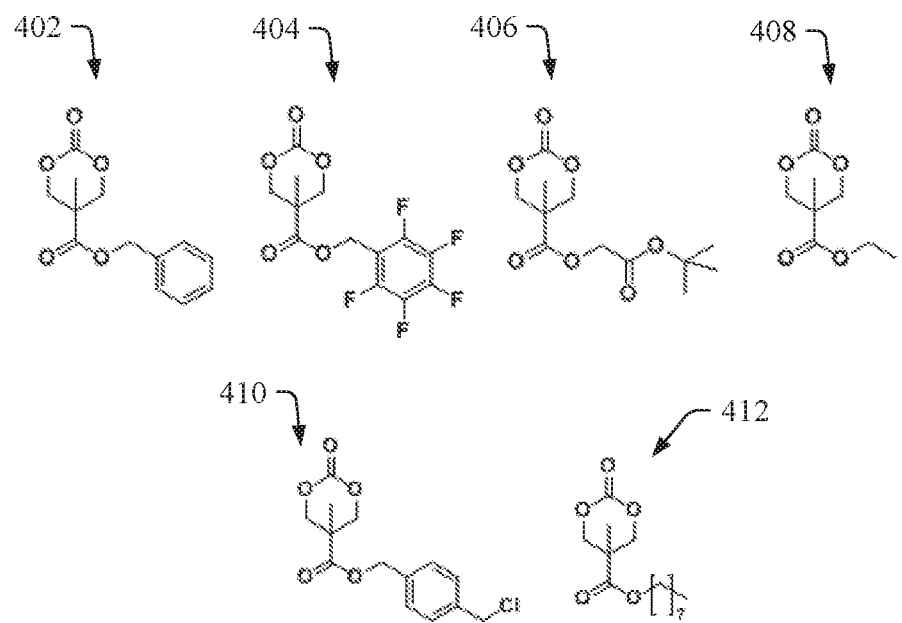
FIG. 4B illustrates a diagram of example, non-limiting functionalized cyclic carbonate monomers that can be synthesized via one or more alkylation-cyclization and/or cyclization-esterification processes in accordance with one or more embodiments described herein.

FIG. 4B illustrates a diagram of example, non-limiting functionalized cyclic carbonate monomer 102 structures that can be achieved via the processes (e.g., alkylation-cyclization processes, such as alkylation scheme 300 and/or cyclization scheme 400) in accordance with one or more embodiments described herein. Repetitive description of like elements employed in other embodiments described herein is omitted for sake of brevity. One of ordinary skill in the art will recognize that the structures depicted in FIG. 4B demonstrate exemplary monomers that can be formed in accordance with the methods, alkylation-cyclization processes, and/or cyclization-esterification processes described herein. However, the variety of monomers that can be synthesized via the methods, alkylation-cyclization processes, and/or cyclization-esterification processes described herein is not limited to the exemplary structures depicted in FIG. 4B.

The following experimental procedure can exemplify synthesis of the first example monomer 402. A solution of benzyl 3-hydroxy-2-(hydroxymethyl)-2-methylpropanoate (e.g., 2.0 grams (g), 9.0 millimoles (mmol)), CDI (e.g., 2.19 g, 13.5 mmol), and MeCN (e.g., 40 mL) can be prepared and stirred at room temperature for 10 min. AcOH (e.g., 8.2 mL, 144 mmol) can be added and the reaction mixture can be stirred at 75° C. for 3.5 hours in a preheated oil bath. After 3.5 hours, the reaction mixture can be removed from the oil bath and allowed to cool to room temperature. Following a general aqueous work-up procedure, the isolated material can be transferred to a 250 mL Erlenmeyer flask and dissolved in a minimal amount of THF (e.g., about 8 mL). The solution can be diluted with 125 mL MTBE and hexanes (e.g., about 50 mL) can be added with agitation until crystals had formed. The slurry can be cooled to −20° C. in a freezer overnight. The slurry can then be filtered, and the filter cake can be washed with cold Et$_2$O (e.g., 2×20 mL) and dried to give the desired product as fluffy white crystals weighing 1.73 g (e.g., 77% yield)

The following experimental procedure can exemplify synthesis of the second example monomer 404. MPA-BnF$_5$ (e.g., 5.19 g, 16.5 mmol) and CDI (e.g., 4.13 g, 25.5 mmol) can be dissolved in MeCN (e.g., 80 mL) to form a reaction mixture. AcOH (e.g., 16 mL, 279.5 mmol) can be added and the reaction mixture can be heated at 75° C. for 1 hour. After 1 hour, the reaction mixture can be removed from the oil bath and allowed to cool to room temperature and then worked-up and purified. The desired product can be isolated as a white crystalline solid (e.g., 4.41 g, 78% yield).

The following experimental procedure can exemplify synthesis of the third example monomer 406. A solution of MPA-CH$_2$CO$_2$—Bu (e.g., 250.7 mg, 1 mmol) and CDI (e.g., 276.2 mg, 1.7 mmol) in MeCN (e.g., 5 mL) can be stirred for 5 minutes. AcOH (e.g., 1 mL, 17.3 mmol) can be added and the reaction mixture was heated at 75° C. for 1.5 h ours. After 1.5 hours, the reaction mixture can be removed from the oil bath and allowed to cool to room temperature and then worked-up and purified. The desired product can be isolated as a white crystalline solid (e.g., 0.22 g, 78% yield).

The following experimental procedure can exemplify synthesis of the fourth example monomer 408. A solution of ethyl 3-hydroxy-2-(hydroxymethyl)-2-methylpropanoate (e.g., 2.0 g, 12.3 mmol), CDI (e.g., 3.4 g 30.0 mmol), and MeCN (e.g., 25 mL) can be stirred at room temperature for 10 minutes. AcOH (e.g., 11.2 mL, 195.7 mmol) can be added and the reaction vessel was then equipped with a reflux condenser and heated to 70° C. in a preheated oil bath for 2 hours. After 2 hours, the reaction mixture can be removed from the oil bath, allowed to cool to, and the reaction mixture can be worked-up and purified to afford the desired product as a white solid weighing 1.91 g (e.g., 82% yield).

The following experimental procedure can exemplify synthesis of the fifth example monomer 410. CDI (e.g., 4.8 g, 29.6 mmol) can be added to a solution of MPA-BnCl (e.g., 4.0 g, 14.7 mmol) in MeCN (e.g., 100 mL) and stirred at room temperature for 10 minutes. AcOH (e.g., 14.0 mL, 244.6 mmol) can then be added and the reaction mixture can be stirred at 70° C. for 2 hours. After 2 hours the reaction mixture can be worked-up and purified. Following purification, the desired product can be isolated as white crystals (e.g., 3.07 g, 70% yield).

The following experimental procedure can exemplify synthesis of the sixth example monomer 412. A solution of MPA-Octyl (e.g., 1.64 g, 6.7 mmol) in MeCN (e.g., 15 mL) can be stirred at room temperature for 10 minutes. AcOH (e.g., 10.0 mL, 158.6 mmol) can then be added and the reaction mixture can be stirred at 70° C. for 2 hours. After 2 hours the reaction mixture can be worked-up. The isolated crude oil can be purified via silica gel column chromatography (e.g., 0-50% EtOAc in hexanes) to afford a colorless oil (e.g., 1.41 g, 78% yield).

Figure 5:
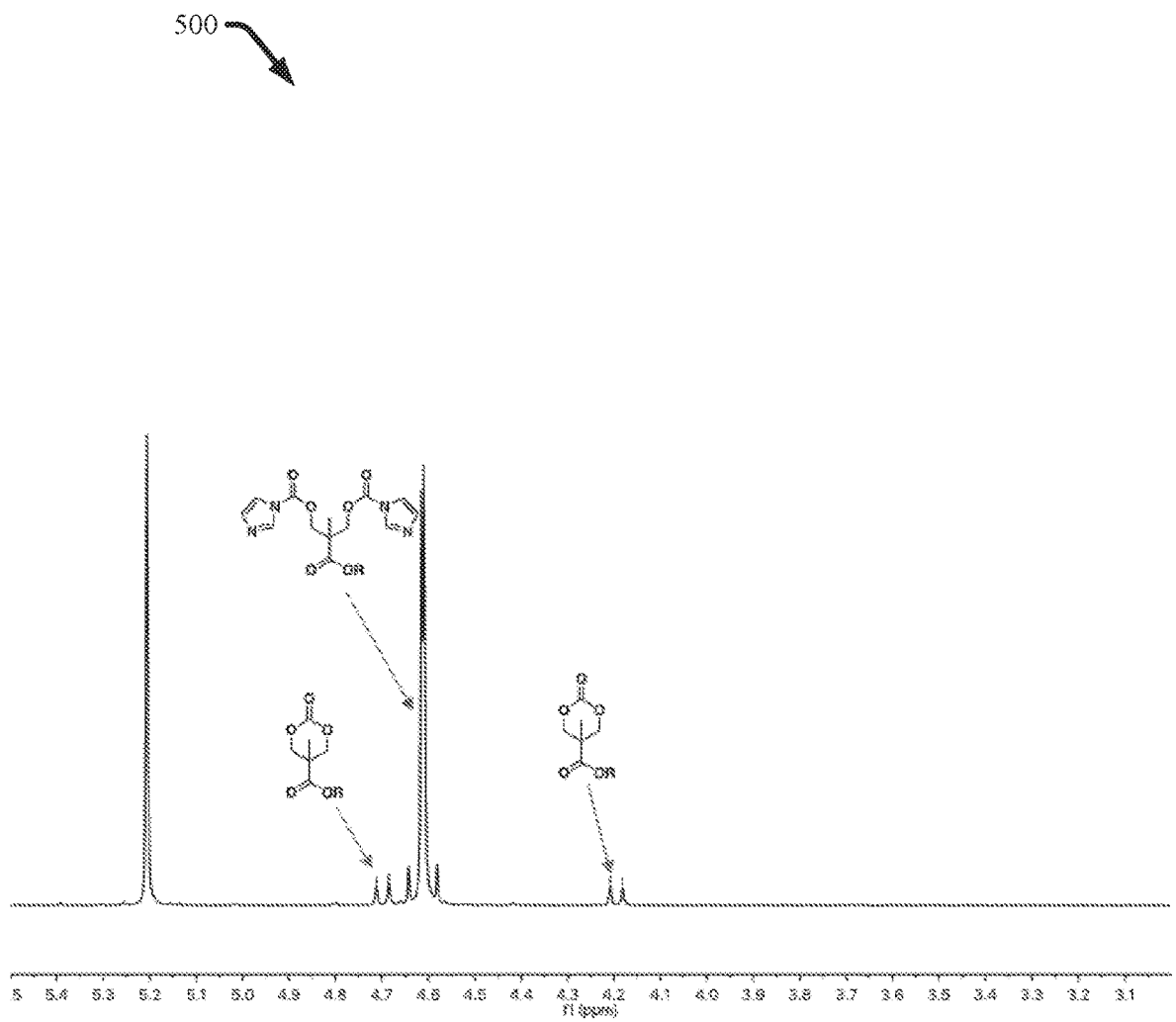
FIG. 5 illustrates a diagram of an example, non-limiting first nuclear magnetic resonance ("NMR") graph regarding a synthesis of a cyclic carbonate monomer from a functionalized diol monomer using CDI in accordance with one or more embodiments described herein.
Figure 6:
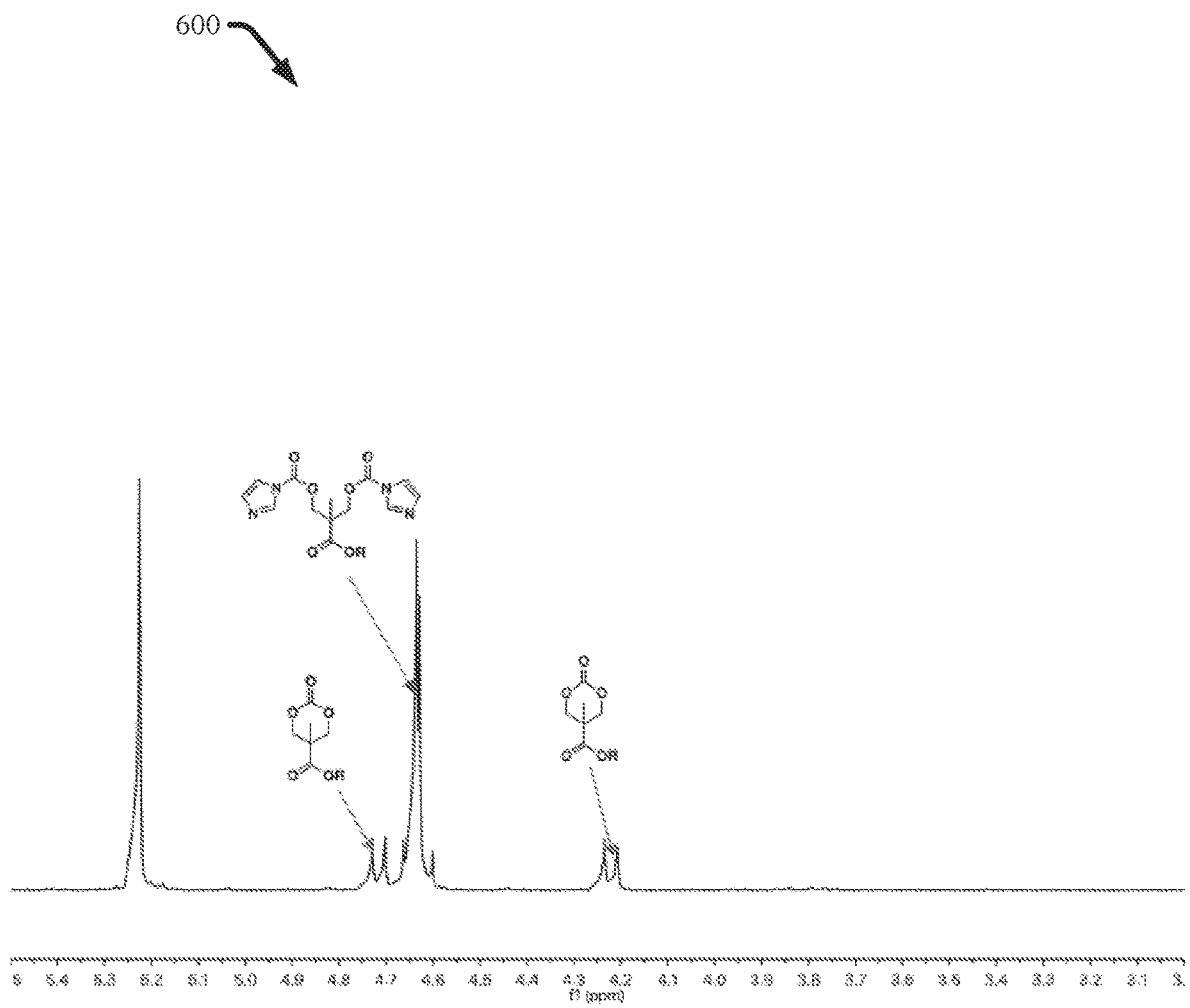
FIG. 6 illustrates a diagram of an example, non-limiting second NMR graph regarding a synthesis of a cyclic carbonate monomer from a functionalized diol monomer using CDI in accordance with one or more embodiments described herein.
Figure 7:
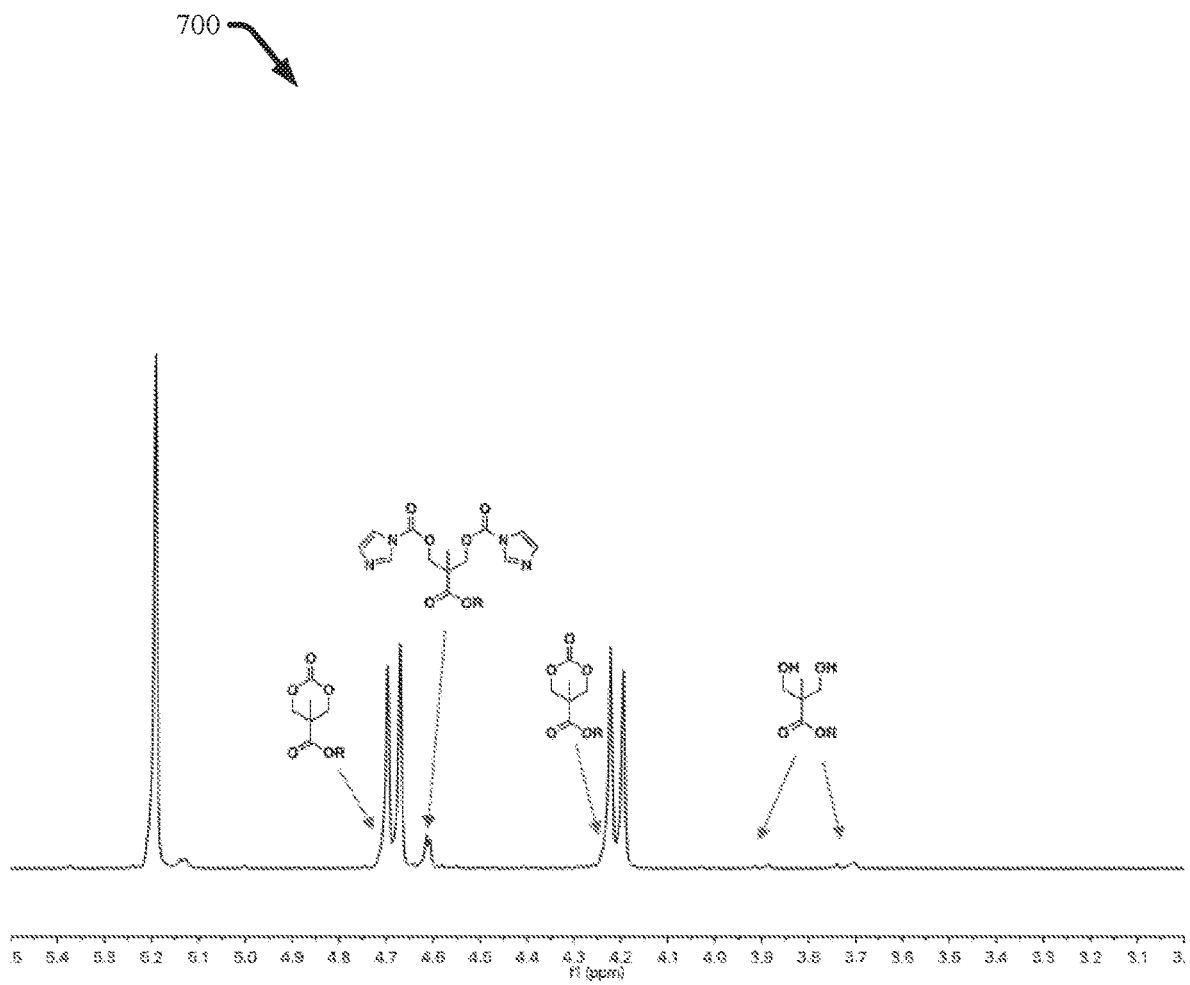
FIG. 7 illustrates a diagram of an example, non-limiting third NMR graph regarding a synthesis of a cyclic carbonate monomer from a functionalized diol monomer using CDI in accordance with one or more embodiments described herein.
Figure 8:
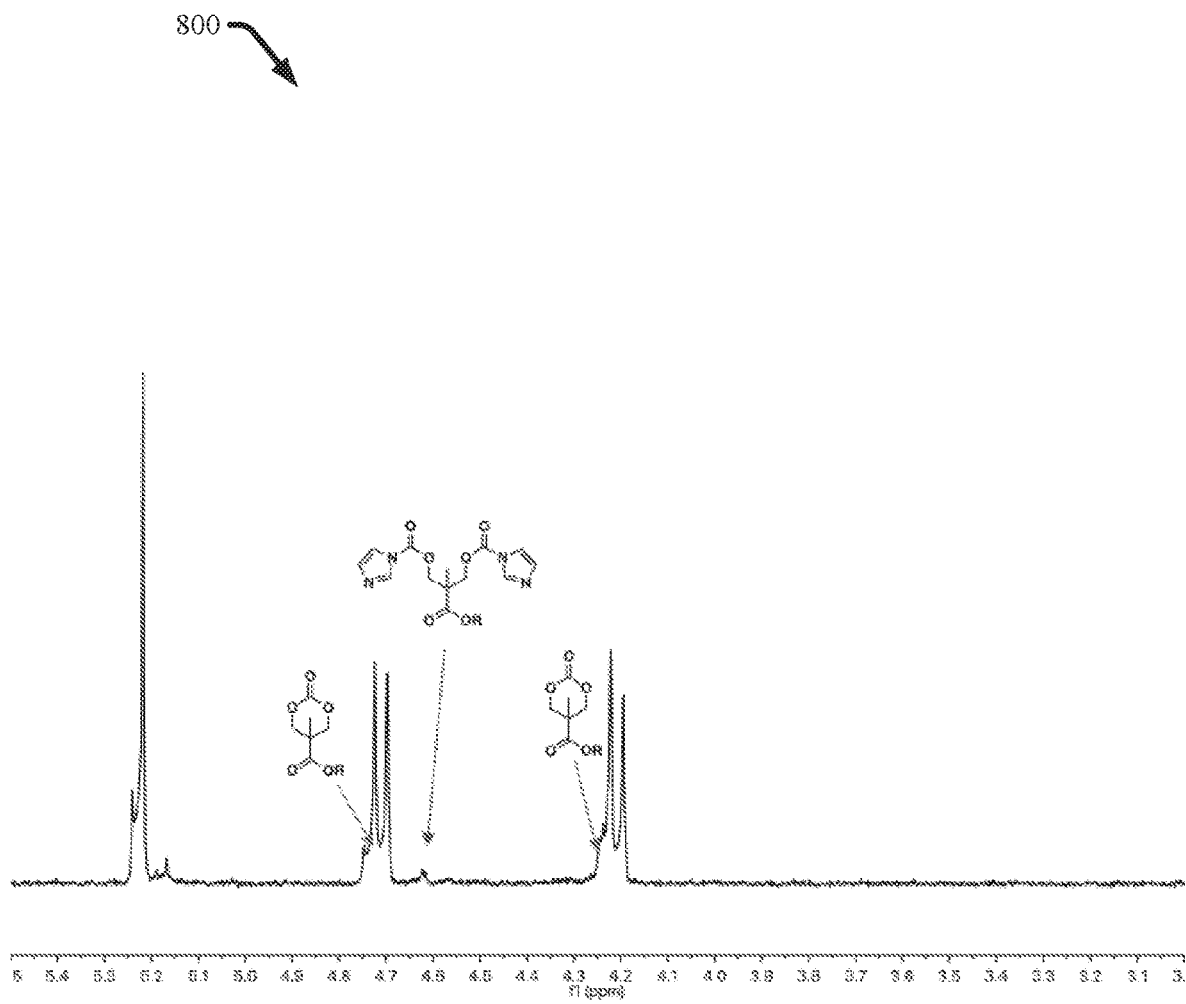
FIG. 8 illustrates a diagram of an example, non-limiting fourth NMR graph regarding a synthesis of a cyclic carbonate monomer from a functionalized diol monomer using CDI in accordance with one or more embodiments described herein.
Figure 9:
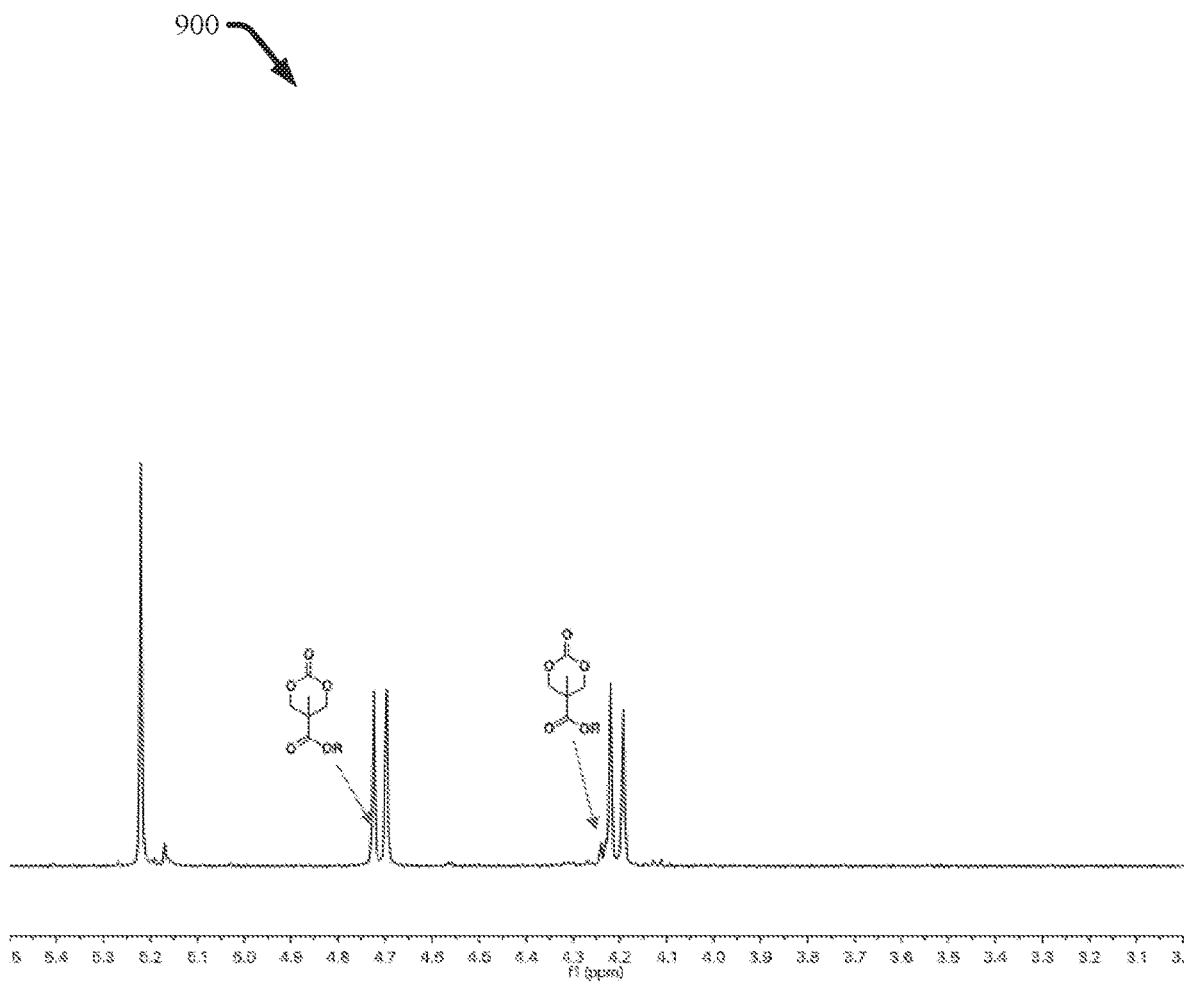
FIG. 9 illustrates a diagram of an example, non-limiting fifth NMR graph regarding a synthesis of a cyclic carbonate monomer from a functionalized diol monomer using CDI in accordance with one or more embodiments described herein.

FIGS. 5-9 illustrate diagrams of example, non-limiting NMR spectra regarding various moments during the first cyclization scheme 400 in accordance with one or more embodiments described herein. Repetitive description of like elements employed in other embodiments described herein is omitted for sake of brevity. FIG. 5 depicts a first NMR spectrum 500 of the first cyclization scheme 400 five minutes after initial addition of CDI. FIG. 6 depicts a second NMR spectrum 600 of the first cyclization scheme 400 ten minutes after addition of 16 equivalents of AcOH at 70° C. FIG. 7 depicts a third NMR spectrum 700 of the first cyclization scheme 400 three hours after addition of 16 equivalents of AcOH at 70° C. FIG. 8 depicts a fourth NMR spectrum 800 of the first cyclization scheme 400 after concentration at room temperature under nitrogen gas stream. FIG. 9 depicts a fifth NMR spectrum 900 of the first cyclization scheme 400 after aqueous workup with 1 M HCl. The NMR spectra depicted in FIGS. 5-9 can demonstrate the efficacy of the first cyclization scheme 400 in cyclizing the one or more functionalized diol monomers 106 to achieve high conversion rates to the functionalized cyclic carbonate monomers 102.

FIG. 10 illustrates a flow diagram of an example, non-limiting method 1000 that can facilitate synthesizing the one or more functionalized cyclic carbonate monomers 102 via the one or more cyclization-esterification processes in accordance with one or more embodiments described herein. Repetitive description of like elements employed in other embodiments described herein is omitted for sake of brevity.

At 1002, the method 1000 can comprise selectively reacting a primary alcohol group of the one or more diol monomers 104 with CDI and an amine base, wherein the reacting at 1002 can form a carbamate amine salt compound. For example, the reacting at 1002 can be facilitated by adding an amine base and CDI to a solution of the one or more diol monomers 104, wherein adding the amine base and CDI can form the carbamate amine salt. As described herein, the one or more diol monomers 104 can comprise at least primary alcohol groups (e.g., hydroxyl groups) and a carboxyl group. In various embodiments, the reacting at 1002 can selectively react the primary alcohol groups over the carboxyl group.

At 1004, the method 1000 can comprise cyclizing the carbamate amine salt compound with an acid, wherein the cyclizing at 1004 can form a non-functionalized cyclic carbonate monomer 108. For example, the cyclizing at 1002 can be facilitated by adding an acid to a solution of the carbamate amine salt compound, wherein adding the acid can form the one or more non-functionalized cyclic carbonate monomers 108. In various embodiments, the acidic conditions contributed by the one or more acids can promote the cyclization of the carbamate amine salt compound.

At 1006, the method 1000 can comprise functionalizing the one or more non-functionalized cyclic carbonate monomers 108 via an esterification of a carboxyl group of the non-functionalized cyclic carbonate monomer 108. In various embodiments, the functionalizing at 1006 can be performed via an esterification with one or more coupling agents.

Figure 11:
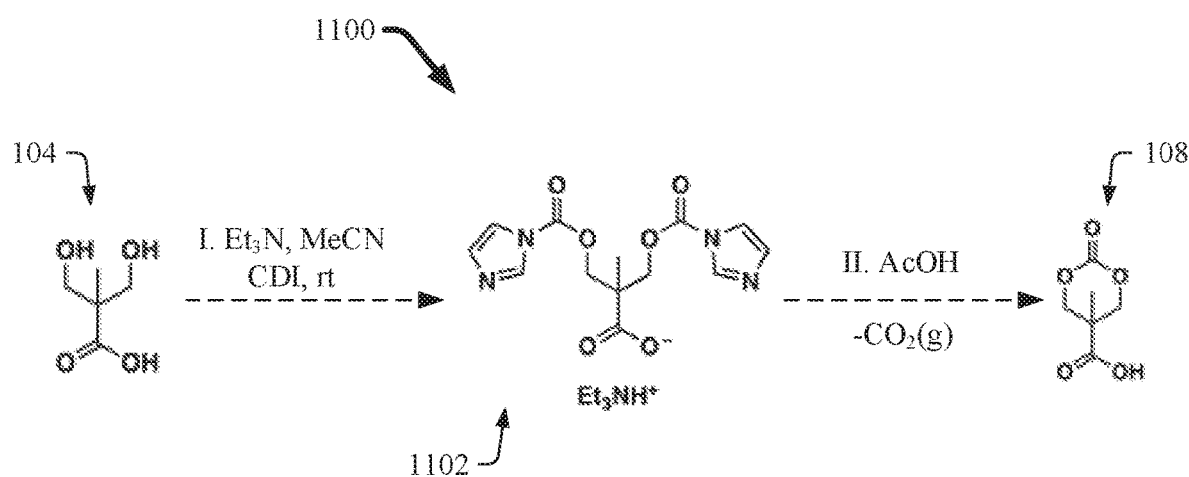
FIG. 11 illustrates a diagram of an example, non-limiting second cyclization scheme that can be comprised within a cyclization-esterification process for the synthesis of cyclic carbonate monomers using CDI in accordance with one or more embodiments described herein.

FIG. 11 illustrates a diagram of an example, non-limiting second cyclization scheme 1100 that can be performed during one or more cyclization-esterification processes to facilitate synthesis of one or more functionalized cyclic carbonate monomers 102 in accordance with one or more embodiments described herein. Repetitive description of like elements employed in other embodiments described herein is omitted for sake of brevity. In various embodiments, the exemplary second cyclization scheme 1100 can be performed during the selective reacting at 1002 and/or the cyclizing at 1004 of method 1000.

As shown in FIG. 11, the second cyclization scheme 1100 can utilize CDI to facilitate selectively reacting the diol of the one or more diol monomers 104. In various embodiments, the second cyclization scheme 1100 can comprise a first stage (e.g., represented by "I." in FIG. 11) where CDI and an amine base can be added to a solution of the one or more diol monomers 104 (e.g., dissolved in MeCN at room temperature). An amount of CDI added to the functionalized diol monomer 106 solution can range, for example, from greater than or equal to 1 equivalents to less than or equal to 3 equivalents (e.g., 2 equivalents). In one or more embodiments, the CDI can be added over a period of time ranging, for example, from greater than or equal to 1 second to less than or equal to 60 minutes. Also, an amount of amine base added to the functionalized diol monomer 106 solution can range, for example, from greater than or equal to 0.5 equivalents to less than or equal to 3 equivalents (e.g., 1 equivalent). Example amine bases that can be utilized to facilitate reaction of the diol monomers 104 with CDI can include, but are not limited to: $Et_3N$, DIEA, 1,1,3,3-tetramethylguanidine, N,N-diethylmethylamine, N,N-dicyclohexylmethylamine, a combination thereof, and/or the like.

The first stage of the second cyclization scheme 1100 can form a carbamate amine salt monomer 1102. In various embodiments, the amine base can deprotonate the carboxyl group of the one or more diol monomers 104 such that the CDI can selectively react with the diol group of the one or more diol monomers 104. For example, the first stage of the second cyclization scheme 1100 can utilize an amine base (e.g., $Et_3N$) to assist in solubilizing the diol monomer 104 (e.g., bis-MPA) in one or more organic solvents, whereupon CDI can be added to the solution to achieve selective conversion of the diol monomer 104 to the carbamate amine salt monomer 1102. Thereby, the amine base can increase the solubility of the diol monomer 104 (e.g., bis-MPA starting material) in organic solvents and decrease the reactivity of the carboxylic acid towards CDI.

Further, a second stage (e.g., represented by "II." In FIG. 11) of the second cyclization scheme 1100 can convert the one or more carbamate amine salt monomers 1102 into one or more non-functionalized cyclic carbonate monomers 108 (e.g., 5-methyl-2-oxo-1,3,-dioxane-5-carboxylic acid, as shown in FIG. 11). During the second stage of the second cyclization scheme 1100 the one or more carbamate amine salt monomers 1102 can be cyclized with excess amounts of acid to promote conversion of the carbamate amine salt monomers 1102 to the non-functionalized cyclic carbonate monomers 108. Additionally, carbon dioxide gas can be liberated during the cyclization. Example acids that can be used in the second stage of the second cyclization scheme 1100 to promote conversion of the one or more carbamate amine salt monomers 1102 can include, but are not limited to: acetic acid ("AcOH"), benzoic acid, trifluoroacetic acid, hydrochloric acid, methanesulfonic acid, p-tolylsulfonic acid pyridinium salt, formic acid, maleic acid, phosphoric acid, trimethylsilyl trifluoromethanesulfonate, a combination thereof, and/or the like. One of ordinary skill in the art will recognize that the amount of acid added to the one or more carbamate amine salt monomers 1102 can vary depending on the type of acid utilized. An example amount of added acid (e.g., AcOH) can be greater than or equal to 0.1 equivalents and less then or equal to 30 equivalents (e.g., 4 equivalents). In one or more embodiments, the acid can be added over a period of time ranging, for example, from greater than or equal to 5 seconds to less than or equal to 1 hour. Following workup and purification, the desired product can be obtained in approximately 50% yield in accordance with various embodiments described herein. In one or more embodiments, the yield can be improved via a solid supported acidic resin (e.g., Amberlyst 15) filtration procedure. This simplified procedure, instead of an aqueous workup, can significantly improve the workup of various embodiments described herein, wherein the purification process can achieve isolated yields between of 80-90%. Advantageously, the non-functionalized cyclic carbonate monomer 108 can be a highly versatile intermediate that can be functionalized into a variety of cyclic carbonate monomers via different esterification approaches.

Figure 12A:
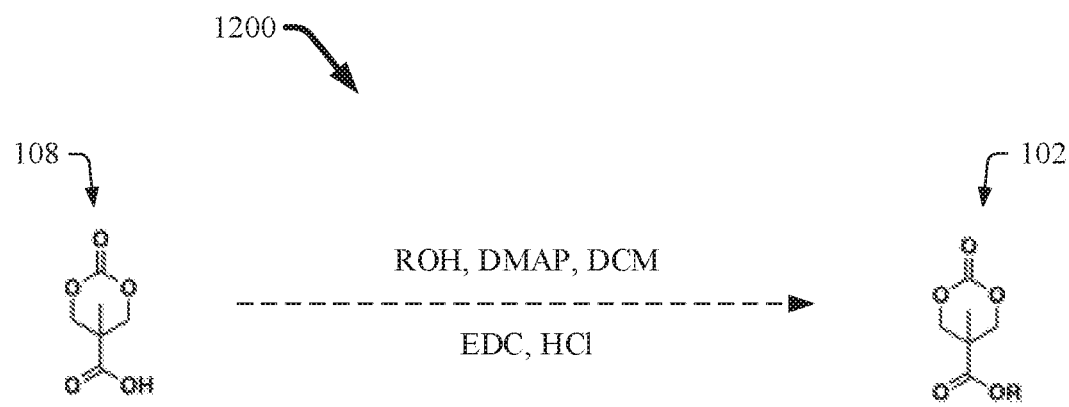
FIG. 12A illustrates a diagram of an example, non-limiting esterification scheme that can that can be comprised within a cyclization-esterification process for the synthesis of functionalized cyclic carbonate monomers in accordance with one or more embodiments described herein.

FIG. 12A illustrates a diagram of an example, non-limiting esterification scheme 1200 that can be performed during one or more cyclization-esterification processes to facilitate synthesis of one or more functionalized cyclic carbonate monomers 102 in accordance with one or more embodiments described herein. Repetitive description of like elements employed in other embodiments described herein is omitted for sake of brevity. In various embodiments, the exemplary esterification scheme 1200 can be performed during the functionalizing at 1006 of method 1000.

The esterification scheme 1200 can facilitate functionalizing the carboxyl group of the one or more non-functionalized cyclic carbonate monomers 108 (e.g., synthesized in accordance with the second cyclization scheme 1100). One of ordinary skill in the art will recognize that the esterification scheme 1200 can incorporate a variety of esterification approaches to facilitate functionalizing the non-functionalized cyclic carbonate monomer 108. FIG. 12A depicts an exemplary esterification approach that utilizes a coupling reaction of the carboxyl group of the non-functionalized cyclic carbonate monomer 108 with an alcohol comprising the target functional group to afford the functionalized cyclic carbonate monomer 102. Example coupling agents that can facilitate the coupling can include, but are not limited to: 1-ethyl-3-(3-dimethylaminopropyl)carbodiimide ("EDC"), N,N'-dicyclohexylcabodiimide, N,N'-disuccinimidyl carbonate, bis(pentafluorophenyl) carbonate, oxalyl chloride, N,N'-diisopropylcarbodiimide, bis(4-nitrophenyl) carbonate, CDI, a combination thereof, and/or the like. In various embodiments, the coupling reaction can be performed at room temperature in non-chlorinated solvents to afford high yields. Additionally, purification can be achieved through filtration of the crude reaction mixture through a silica gel plug to remove coupling agent (e.g., EDC) byproducts As shown in FIG. 12A, the one or more alcohols that can be utilized in the esterification can be represented by "ROH", wherein "R" can represent the target functional group. Example alcohols can include, but are not limited to: 9-anthracene methanol, tert-butyl (E)-(N-(tert-butoxycarbonyl)-N'-(2-hydroxyethyl)carbamimidoyl)-12-azanecarboxylate, 1-(2-hydroxyethyl)-3-phenylurea, 2-(tritylthio)ethan-1-ol, methanol, ethanol, 1-butanol, 1-octanol, 9-fluorenemethanol, tert-butanol, 1-adamantanol, isopropanol, cyclohexanol, benzyl alcohol, allyl alcohol, propargyl alcohol, poly(ethylene glycol) methyl ester, triethylene glycol, 1-pyrenemethanol, a combination thereof, and/or the like. Alternatively, other nucleophiles such as amines or thiols can be used in place of alcohols to provide the corresponding amide or thioester respectively. Example amines and thiols can include, but are not limited to: benzyl mercaptan, butyl 3-mercaptopropionate, anline, diethylamine, morpholine, piperdine, ethyl amine, allyl amine, butyl amine, N-methylanline, a combination thereof, and/or the like. An example time period for the esterification can be greater than or equal to 20 minutes and less than or equal to 18 hours (e.g., 8 hours).

Figure 12B:
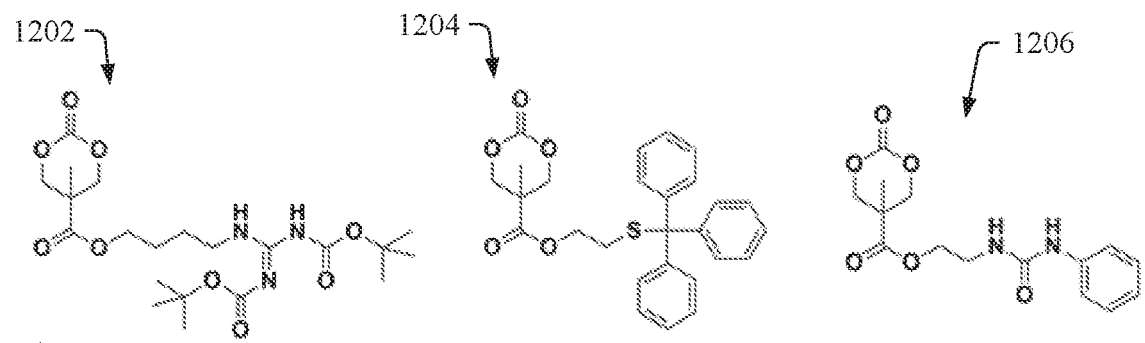
FIG. 12B illustrates a diagram of example, non-limiting functionalized cyclic carbonate monomers that can be synthesized via an alkylation-cyclization and/or cyclization-esterification process in accordance with one or more embodiments described herein.

FIG. 12B illustrates a diagram of example, non-limiting functionalized cyclic carbonate monomer 102 structures that can be achieved via the one or more alkylation-cyclization processes (e.g., alkylation scheme 300 and/or first cyclization scheme 400) and/or cyclization-esterification processes (e.g., second cyclization scheme 1100 and/or esterification scheme 1200) in accordance with one or more embodiments described herein. Repetitive description of like elements employed in other embodiments described herein is omitted for sake of brevity. One of ordinary skill in the art will recognize that the structures depicted in FIG. 12B demonstrate exemplary monomers that can be formed in accordance with the methods, alkylation-cyclization processes, and/or cyclization-esterification processes described herein. However, the variety of monomers that can be synthesized via the methods, alkylation-cyclization processes, and/or cyclization-esterification processes described herein is not limited to the exemplary structures depicted in FIG. 12B.

The following experimental procedure can exemplify synthesis of the seventh example monomer 1202. HO-nBuGuaBoc (e.g., 1.38 g 4.2 mmol), MTC (e.g., 1.00 g 6.2 mmol) and DMAP (51 mg, 0.4 mmol) can be dissolved in dichloromethane ("DCM")(e.g., 50 mL). EDC.HCl (e.g., 1.20 g, 6.3 mmol) can be added to facilitate the one or more esterification processes described herein. After the workup procedure, the desired product can be isolated as a white crystalline solid (e.g., 1.85 g, 94% yield).

The following experimental procedure can exemplify synthesis of the eighth example monomer 1204. HO-EtSTrt (e.g., 1.56 g, 4.9 mmol), MTC (e.g., 1.17 g, 7.3 mmol) and 4-dimethylaminopyridine ("DMAP")(e.g., 64.5 mg, 0.5 mmol) can be dissolved in DCM (e.g., 50 m L). EDC.HCl (e.g., 1.43 g, 7.5 mmol) can be added to facilitate the one or more esterification processes described herein. After the workup procedure, the desired product can be isolated as a white crystalline solid (e.g., 1.78 g, 79% yield).

The following experimental procedure can exemplify synthesis of the eighth example monomer 1206. HO-EtUreaPh (e.g., 1.00 g, 5.5 mmol), MTC (e.g., 1.35 g, 8.4 mmol) and DMAP (e.g., 95.2 mg, 0.8 mmol) can be dissolved in DCM (e.g., 50 mL). EDC.HCl (e.g., 1.60 g, 8.3 mmol) can be added to facilitate the one or more esterification processes described herein. After the workup procedure, the desired product can be isolated as a white crystalline solid (e.g., 1.47 g, 82% yield).

Figure 13:
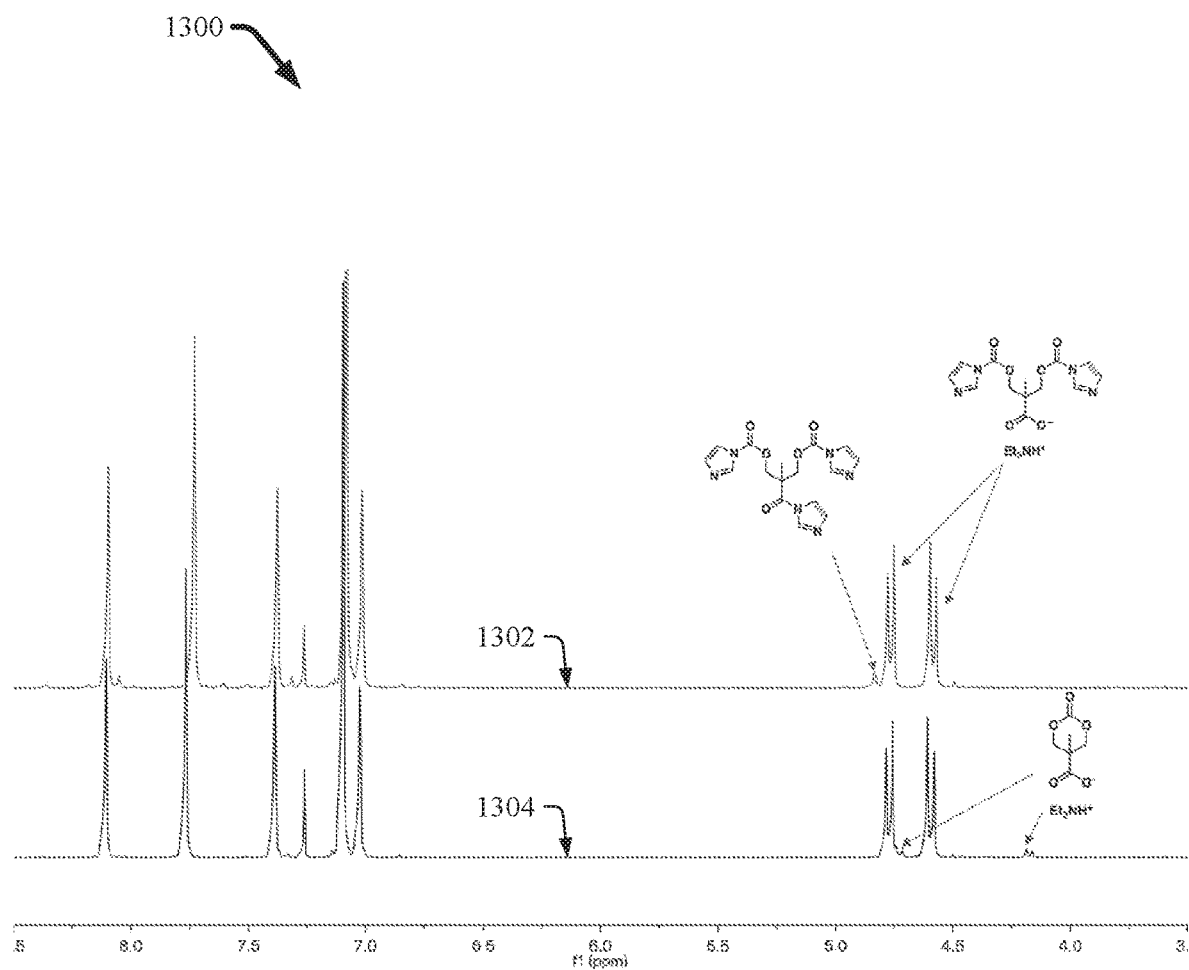
FIG. 13 illustrates a diagram of an example, non-limiting sixth NMR graph regarding a synthesis of a functionalized cyclic carbonate monomer from a diol monomer using CDI in accordance with one or more embodiments described herein.

FIG. 13 illustrates a diagram of an example, non-limiting sixth NMR spectrum 1300 that can demonstrate the efficacy of the one or more second cyclization schemes 1100 in accordance with one or more embodiments described herein. Repetitive description of like elements employed in other embodiments described herein is omitted for sake of brevity. The first line 1302 of the sixth NMR spectrum 1300 can regard selective functionalization of the non-functionalized cyclic carbonate monomer 108 with 2.4 equivalents of CDI for 5 minutes. The second line 1304 of the sixth NMR spectrum 1300 can regard selective functionalization of the non-functionalized cyclic carbonate monomer 108 with 2.4 equivalents of CDI for 5 minutes.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

It is, of course, not possible to describe every conceivable combination of components, products and/or methods for purposes of describing this disclosure, but one of ordinary skill in the art can recognize that many further combinations and permutations of this disclosure are possible. Furthermore, to the extent that the terms "includes," "has" "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, comprising:
cyclizing a functionalized diol monomer with N,N'-carbonyldiimidazole, wherein the cyclizing produces a mixture of a cyclic carbonate monomer and an imidazole carbamate product; and
activating the imidazole carbamate product with an acid, wherein the activating promotes cyclization of the imidazole carbamate product into the cyclic carbonate monomer.

2. The method of claim 1, wherein the N,N'-carbonyldiimidazole is added to a solution of the functionalized diol monomer over a period of time ranging from greater than or equal to 1 second and less than or equal to 60 minutes.

3. The method of claim 1, wherein an amount of the N,N'-carbonyldiimidazole added to a solution of the functionalized diol monomer to perform the cyclizing ranges from greater than or equal to 0.1 equivalents and less than or equal to 3 equivalents.

4. The method of claim 1, wherein the functionalized diol monomer is functionalized 3-hydroxy-2-(hydroxymethyl)-2-methylpropanoic acid.

5. The method of claim 1, further comprising:
reacting a diol monomer using a base compound, wherein the reacting promotes functionalization of the diol monomer with a substrate having a reactive functional group, wherein the substrate is at least one member selected from the group consisting of an alkyl halide, a benzylic halide, an allylic halide, a sulfonate, a carbonate, an ester, a carbamate, and a phosphonate.

6. The method of claim 5, wherein the functionalized diol monomer is functionalized 3-hydroxy-2-(hydroxymethyl)-2-methylpropanoic acid.

7. The method of claim 5, wherein the base compound is at least one compound selected from the group consisting of an amine base, a carbonate base, a phosphate base, a carbonate base, a hydroxide base, and an alkoxide base.

8. The method of claim 1, wherein the functionalized diol monomer is characterized by a structure selected from the group consisting of

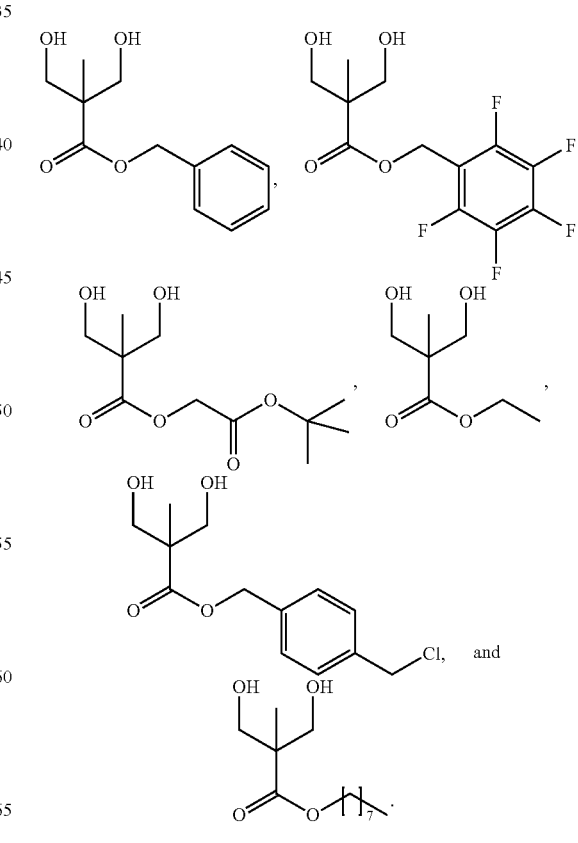

9. A method comprising:
- selectively reacting a primary alcohol group of a diol monomer with N,N'-carbonyldiimidazole and an amine base, wherein the selectively reacting forms a carbamate amine salt compound; and
- cyclizing the carbamate amine salt compound with an acid, wherein the cyclizing forms a cyclic carbonate monomer.

10. The method of claim 9, wherein an amount of the N,N'-carbonyldiimidazole added to a solution of the diol monomer to react with the primary alcohol ranges from greater than or equal to 1 equivalents and less than or equal to 3 equivalents.

11. The method of claim 10, wherein the diol monomer is 3-hydroxy-2-(hydroxymethyl)-2-methylpropanoic acid, wherein the amine base is triethylamine, and wherein the acid is acetic acid.

12. The method of claim 11, wherein an amount of the amine base added to a solution of the diol monomer to perform the reacting ranges from greater than or equal to 0.5 equivalents and less than or equal to 3 equivalents, and wherein an amount of the acid added to a solution of the carbamate amine salt compound to perform the cyclizing ranges from greater than or equal to 0.1 equivalents and less than or equal to 30 equivalents.

13. The method of claim 10, further comprising:
- purifying the cyclic carbonate monomer via a solid supported acidic resin filtration procedure.

14. The method of claim 10, wherein the diol monomer is 3-hydroxy-2-(hydroxymethyl)-2-methylpropanoic acid, and wherein the carbamate amine salt compound is characterized by formula 1:

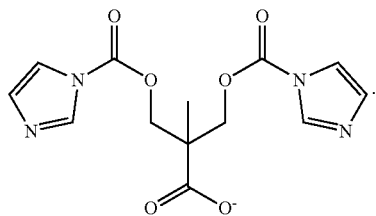 [SMILES: CC(COC(=O)n1ccnc1)(COC(=O)n1ccnc1)C(=O)[O-]]

15. The method of claim 9, further comprising:
- functionalizing the cyclic carbonate monomer via an esterification of a carboxyl group of the cyclic carbonate monomer.

16. A method comprising:
- adding an amine base and N,N'-carbonyldiimidazole to a solution of a diol monomer, wherein adding the amine base and the N,N'-carbonyldiimidazole forms a carbamate amine salt; and
- adding an acid to a solution of the carbamate amine salt, wherein adding the acid forms a cyclic carbonate monomer via cyclization.

17. The method of claim 16, further comprising:
- functionalizing the cyclic carbonate monomer via an esterification of a carboxyl group of the cyclic carbonate monomer.

18. The method of claim 16, wherein the diol monomer is 3-hydroxy-2-(hydroxymethyl)-2-methylpropanoic acid.

19. The method of claim 16, wherein the N,N'-carbonyldiimidazole selectively reacts with a primary alcohol group of the diol monomer over a carboxyl group of the diol monomer to form the carbamate amine salt.

* * * * *